(12) United States Patent
Lin et al.

(10) Patent No.: US 11,607,678 B1
(45) Date of Patent: Mar. 21, 2023

(54) SURFACE SUPPORTED CATALYSTS WITH PORE SIZE CONTROL

(71) Applicant: Saudi Arabian Oil Company, Dhahran (SA)

(72) Inventors: Sibo Lin, Arlington, MA (US); Brian Hanna, Cambridge, MA (US)

(73) Assignee: Saudi Arabian Oil Company, Dhahran (SA)

( * ) Notice: Subject to any disclaimer, the term of this patent is extended or adjusted under 35 U.S.C. 154(b) by 64 days.

(21) Appl. No.: 17/405,616

(22) Filed: Aug. 18, 2021

(51) Int. Cl.
| | |
|---|---|
| *B01J 31/16* | (2006.01) |
| *B01J 21/18* | (2006.01) |
| *B01J 21/08* | (2006.01) |

(52) U.S. Cl.
CPC ........... *B01J 31/1616* (2013.01); *B01J 21/08* (2013.01); *B01J 21/185* (2013.01)

(58) Field of Classification Search
CPC ....... B01J 21/08; B01J 21/185; B01J 31/1616
See application file for complete search history.

(56) References Cited

U.S. PATENT DOCUMENTS

| | | | |
|---|---|---|---|
| 5,648,508 | A | 7/1997 | Yaghi |
| 6,544,923 | B1 | 4/2003 | Ying et al. |
| 7,541,413 | B2 | 6/2009 | Crowther et al. |
| 8,338,325 | B2 | 12/2012 | Brophy et al. |
| 8,889,581 | B2 | 11/2014 | Lee et al. |
| 2009/0048467 | A1 | 2/2009 | Zhou et al. |

FOREIGN PATENT DOCUMENTS

| | | | | |
|---|---|---|---|---|
| EP | 2614887 | * | 7/2013 | .............. B01J 31/24 |
| WO | WO2003/042131 | * | 5/2003 | .............. C07B 31/00 |
| WO | 2009005562 A1 | | 1/2009 | |
| WO | 2012004352 A2 | | 1/2012 | |

OTHER PUBLICATIONS

Britovsek, G.J.P. et al., 1999, Journal of the American Chemical Society, 121, 8728-8740. (Year: 1999).*
Cheng et al., "Ethylene polymerization using silica-supported zirconocene dibromide/methylalumoxane catalysts", Journal of Molecular Catalysis A: Chemical, vol. 212, pp. 121-126, 2004.

(Continued)

*Primary Examiner* — Brian A McCaig
(74) *Attorney, Agent, or Firm* — Dinsmore & Shohl LLP

(57) ABSTRACT

Supported catalysts include a solid support, a metal-ligand complex tethered to a surface of the solid support through at least two surface reactive moieties of the metal-ligand complex, and a conformationally stable molecular pore defined between the metal-ligand complex and the surface of the solid support. The metal-ligand complex includes a catalytic metal center, such as a transition metal, coordinated with multiple monodentate ligands, a multidentate ligand, or a combination thereof. The ligands include a tethering portion that is terminated by a surface reactive moiety tethered to the surface of the solid support by a surface interaction. By tailoring the tethering portion, a volume of the molecular pore may be provided that is selective and suitable for a chosen reactant or a chosen reaction type.

17 Claims, 5 Drawing Sheets

(56) References Cited

OTHER PUBLICATIONS

Lee et al., "Preparation of Anchored Metallocene Complexes on Dehydroxylated Silica and Their Use in the Polymerization of Ethylene", Macromolecules, vol. 33, pp. 3194-3195, 2000.

Small, "Discovery and Development of Pyridine-bis(imine) and Related Catalysts for Olefin Polymerization and Oligomerization", American Chemical Society, vol. 48, pp. 2599-2611, 2015.

Zheng et al., "Ethylene polymerization with silica-supported bis(imino)pryidyl iron (II) catalysts", Journal of Catalysis, vol. 234, pp. 101-110, 2005.

\* cited by examiner

SURFACE SUPPORTED CATALYSTS WITH PORE SIZE CONTROL

TECHNICAL FIELD

The present disclosure relates to transition metal complexes and supported catalysts including the transition-metal complexes.

BACKGROUND

Synthetic molecular transition metal catalysts commonly utilized in industry tend to have limited enclosure of the reaction cavity and limited reaction selectivity. While rigid and bulky substituents can be incorporated into catalyst ligands to construct a reaction hemi-cavity, it is generally not synthetically feasible to encase an entire reaction cavity in a molecularly defined framework. In one exception, metal organic frameworks (MOFs) possess molecularly defined pores that can act as reaction cavities and screen out larger substrates from reaction with interior catalyst sites. However, MOFs have limited chemical, steric, and size tunability, and significant effort is often required to develop new MOFs. Additionally, if substrates and products are controlled by the sizes of the MOF pores, then diffusion to interior MOF sites will be hindered. Inorganic zeolites have molecularly-sized pores but are not synthetically tunable with molecular precision in same manner as organic and metal-organic catalysts.

SUMMARY

Ongoing needs exist for methods of defining a reaction cavity on a molecular level that is applicable to catalyst reactions for which greater selectivity toward a specific product is a goal. Molecularly tunable reaction cavities would be of particular interest for many industrial-scale applications include, but not limited to, olefin hydrogenation, epoxidation, hydroformylation, and and various levels of polymerizations such as dimerizations, trimerizations, and oligomerizations.

In view of these needs, example embodiments disclosed herein are directed to supported catalysts. The supported catalysts include a solid support, a metal-ligand complex tethered to a surface of the solid support through at least two surface reactive moieties of the metal-ligand complex, and a conformationally stable molecular pore defined between the metal-ligand complex and the surface of the solid support. The metal-ligand complex tethered to the surface of the solid support has formula (I):

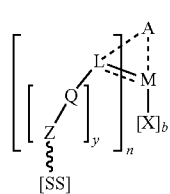

(I)

In formula (I), SS is the solid support; M is a catalytic metal center chosen from transition metals; the metal-ligand complex has an activated form and a precatalyst form; b is 0 in the activated form of the metal-ligand complex; b is 1, 2, or 3 in the precatalyst form of the metal-ligand complex, wherein each X is a leaving group chosen from halogens, monodentate ligands, and bidentate ligands; n is 2, 3, or 4; each L is a ligating portion independently chosen from a monodentate ligating portion coordinated once to the catalytic metal center and a bidentate ligating portion coordinated twice to the catalytic metal center; A is absent or is a connecting portion that is covalently bonded to at least two of the ligating portions L and optionally is coordinated to the catalytic metal center M; y is 1 or 2; each Q is a divalent tethering portion independently chosen from $C_6$—$C_{40}$ hydrocarbylene or $C_6$—$C_{40}$ heterohydrocarbylene, wherein the $C_6$—$C_{40}$ hydrocarbylene or $C_6$—$C_{40}$ heterohydrocarbylene is substituted or unsubstituted; and each Z is independently a surface reactive moiety tethered to the surface of the solid support by at least one surface interaction between an atom of the surface reactive moiety and the surface.

These and other features, aspects, and advantages will become better understood with reference to the following description and the appended claims.

Additional features and advantages of the embodiments described herein will be set forth in the detailed description that follows, and in part will be readily apparent to those skilled in the art from that description or recognized by practicing the embodiments described herein, including the detailed description that follows, the claims, as well as the appended drawings.

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate the various embodiments described herein, and together with the description serve to explain the principles and operations of the claimed subject matter.

DETAILED DESCRIPTION

Figure 1A:
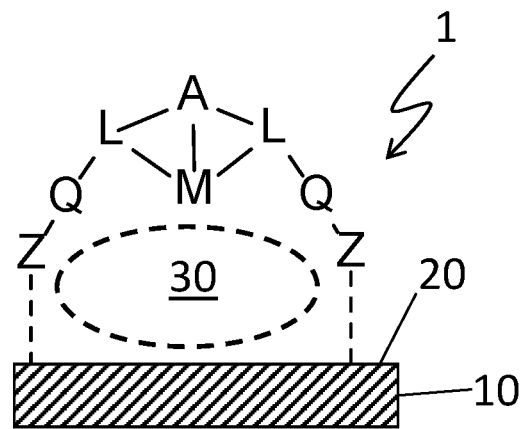
FIGS. 1A-1C are general examples of supported catalysts having two ligating portions, according to embodiments of this disclosure.

The term "independently selected" is used herein with respect to variable chemical groups to indicate that the variable groups may be identical or different, without regard to the identity of any other variable group.

When used to describe certain carbon atom-containing chemical groups, a parenthetical expression having the form "$(C_x—C_y)$" means that the unsubstituted form of the chemical group has from x carbon atoms to y carbon atoms, inclusive of x and y. For example, a $(C_1—C_{50})$ alkyl is an alkyl group having from 1 to 50 carbon atoms in its unsubstituted form. In some embodiments and general structures, certain chemical groups may be substituted by one or more substituents. A substituted chemical group defined using the "$(C_x—C_y)$" parenthetical may contain more than y carbon atoms depending on the identity of any substituents. For example, a "$(C_1—C_{50})$ alkyl substituted with exactly one phenyl (—$C_6H_5$)" may contain from 7 to 56 carbon atoms. Thus, in general when a chemical group defined using the "$(C_x—C_y)$" parenthetical is substituted by one or more carbon atom-containing substituents, the minimum and maximum total number of carbon atoms of the chemical group is determined by adding to both x and y the combined sum of the number of carbon atoms from all of the carbon atom-containing substituents.

The term "substitution" means that at least one hydrogen atom (—H) bonded to a carbon atom or heteroatom of a corresponding unsubstituted compound or functional group is replaced by a substituent. Substituents may be any chemical functional group or radical that could replace a hydrogen atom bonded to a carbon atom or heteroatom of a corresponding unsubstituted compound.

The term "—H" means a hydrogen or hydrogen radical that is covalently bonded to another atom. "Hydrogen" and "—H" are interchangeable, and unless clearly specified have identical meanings.

Except as noted otherwise, the term "hydrocarbon" includes unsubstituted hydrocarbons and substituted hydrocarbons. Unsubstituted hydrocarbons are compounds consisting of carbon atoms and hydrogen atoms. Substituted hydrocarbons are compounds resulting from replacing at least one hydrogen atom of an unsubstituted hydrocarbon with a substituent atom or chemical group. Hydrocarbons may be straight-chain, or branched, aromatic, non-aromatic, cyclic, acyclic, saturated, or unsaturated.

The term "heterohydrocarbon" means a compound resulting from replacing at least one carbon atom, but fewer than all carbon atoms, of an unsubstituted hydrocarbon or a substituted hydrocarbon with a heteroatom. Non-limiting examples of heteroatoms include oxygen, nitrogen, sulfur, and phosphorus.

The term "hydrocarbyl" means a monovalent radical resulting from removal of any hydrogen atom from a hydrocarbon, including aromatic hydrocarbons, non-aromatic hydrocarbons, cyclic or acyclic hydrocarbons, saturated or unsaturated hydrocarbons, straight chain or branched chain hydrocarbons, and substituted or unsubstituted hydrocarbons.

The term "hydrocarbylene" means a divalent radical resulting from removal of any two hydrogen atoms from a hydrocarbon, including aromatic hydrocarbons, non-aromatic hydrocarbons, cyclic or acyclic hydrocarbons, saturated or unsaturated hydrocarbons, straight chain or branched chain hydrocarbons, and substituted or unsubstituted hydrocarbons.

The term "heterohydrocarbyl" means a monovalent radical resulting from removal of any hydrogen atom from a heterohydrocarbon.

The term "heterohydrocarbylene" means a divalent radical resulting from removal of any two hydrogen atoms from a heterohydrocarbon.

The term "aryl" means a monovalent aromatic hydrocarbon radical, in which the carbon atoms of the aromatic system may be substituted or unsubstituted.

The term "arylene" means a divalent aromatic hydrocarbon radical, in which the carbon atoms of the aromatic system may be substituted or unsubstituted. Non-limiting examples of arylenes include substituted or unsubstituted 1,4-phenylene, substituted or unsubstituted 1,3-phenylene, and substituted or unsubstituted 1,2-phenylene.

The term "alkyl" means a monovalent radical resulting from removal of one hydrogen atom from a saturated hydrocarbon radical that may be straight-chain or branched. Accordingly, the term "$(C_1—C_{20})$ alkyl" means a saturated straight or branched hydrocarbon radical of from 1 to 20 carbon atoms that is unsubstituted or substituted. Examples of unsubstituted $(C_1—C_{20})$ alkyl include methyl; ethyl; 1-propyl; 2-propyl; 1-butyl; 2-butyl; 2-methylpropyl; 1,1-dimethylethyl; 1-pentyl; 1-hexyl; 1-heptyl; 1-nonyl; and 1-decyl. Examples of substituted $(C_1—C_{20})$ alkyl include trifluoromethyl and trifluoroethyl.

The term "alkylene" means a divalent saturated hydrocarbon radical that may be straight-chain or branched. Accordingly, the term "$(C_1—C_{20})$ alkyl" means a saturated straight or branched hydrocarbon radical of from 1 to 20 carbon atoms that is unsubstituted or substituted. Examples of unsubstituted $(C_1—C_{20})$ alkyl include methyl; ethyl; 1-propyl; 2-propyl; 1-butyl; 2-butyl; 2-methylpropyl; 1,1-dimethylethyl; 1-pentyl; 1-hexyl; 1-heptyl; 1-nonyl; and 1-decyl. Examples of substituted $(C_1—C_{20})$ alkyl include trifluoromethyl and trifluoroethyl.

The term "cycloalkyl" means a saturated cyclic hydrocarbon radical. Accordingly, the term "$(C_3—C_{20})$ cycloalkyl" means a saturated cyclic hydrocarbon radical of from 3 to 20 carbon atoms that is unsubstituted or substituted. Other cycloalkyl groups (e.g., $(C_x—C_y)$ cycloalkyl) are defined in an analogous manner as having from x to y carbon atoms and being either unsubstituted or substituted. Non-limiting examples of $(C_3—C_{40})$ cycloalkyl include cyclopropyl, cyclobutyl, cyclopentyl, cyclohexyl, cycloheptyl, cyclooctyl, cyclononyl, and cyclodecyl, any of which may be substituted or unsubstituted.

The term "amine" means a compound having the general structure —$NR^1R^2$ where R is independently selected from —H and substituted or unsubstituted, linear or branched hydrocarbyl or heterohydrocarbyl. Amines may be primary amines, secondary amines and tertiary amines. When $R^1$ and $R^2$ are both —H, the amine is a primary amine. When either $R^1$ or $R^2$ but not both are —H, the amine is a secondary amine. When neither $R^1$ nor $R^2$ is —H, the amine is a tertiary amine. The term "alkyl amine" means an amine where either $R^1$ or $R^2$ or both $R^1$ and $R^2$ are alkyl, such as methyl or ethyl, for example.

The term "saturated" means lacking carbon-carbon double bonds, carbon-carbon triple bonds, and (in heteroatom-containing groups) carbon-nitrogen, carbon-phosphorous, and carbon-silicon double bonds. Where a saturated chemical group is substituted by one or more substituents, one or more double and/or triple bonds optionally may be present in substituents. The term "unsaturated" means containing one or more carbon-carbon double bonds or carbon-carbon triple bonds, or (in heteroatom-containing groups) one or more carbon-nitrogen double bonds, carbon-phosphorous double bonds, or carbon-silicon double bonds, not including double bonds that may be present in substituents, if any, or in aromatic rings or heteroaromatic rings, if any.

Supported catalysts according to this disclosure are designed to create nanometer-scale pore-size control for catalytic reactions. The supported catalysts are prepared in suspension by reacting a molecular, multidentate transition metal catalyst with a surface or a solid support. Owing to the chemical configuration of the catalyst, a molecule-sized pore is defined by the transition metal catalyst, two or more flanking surface-reactive moieties, and the surface. The physical and chemical characteristics of the pore may be tuned by tailoring the structure of the supporting ligands on the catalyst or by choice of the solid support itself surface. Furthermore, the catalytically active coordination sites of the transition metal center are confined within this cavity. Thereby, finer control of catalytic processes using the supported catalysts herein is possible that is not available from solution-phase small molecule catalysts.

In general, the supported catalysts of this disclosure are designed according to several basic principles. Foremost, the supported catalysts include a metal-ligand complex tethered to a solid support, and a fixed molecular pore or cavity is defined between the metal-ligand complex and the solid support. The metal-ligand complex itself includes a catalytically active metal center or a metal center that can be made catalytically active upon removal of leaving groups bonded to or coordinated with the metal center. The metal center is generally surrounded by a ligand structure including at least two ligating atoms that coordinate with the metal center.

The ligand structure as a whole may include essentially any defined organic structure that coordinates with the metal center. However, to establish the fixed molecular pore, the ligand structure is further designed to include tethering portions that extend outwardly away from a core of the ligand structure where the metal coordination occurs. The tethering portions are designed to substantially limit or exclude chemical structures such as single bonds that enable the tethering portions to rotate, bend, or sway. Thereby, the tethering portions function as rigid legs or columns to the ligand structure and are terminated by a surface reactive atom or a surface reactive chemical moiety. These surface reactive atoms or moieties interact easily and strongly with the surface of the solid support or with functional groups present on the surface of the solid support.

When the metal-ligand complex is supported onto or tethered onto the solid support through multiple surface reactive atoms or moieties, the metal-ligand complex is fixed in position in the plane of the surface of the solid support. Furthermore, the rigidity of the multiple tethering portions stabilizes the conformational position and orientation of the metal-ligand catalyst so that the active sites of the metal center are consistently oriented toward the surface of the solid support. Thereby, a molecular pore defined between the metal-ligand complex and the solid support may have a substantially fixed volume, a substantially fixed conformation, and a substantially fixed distance between the active metal and the solid support.

In view of the foregoing general description, embodiments of supported catalysts will now be described, with reference to the drawings.

The supported catalyst includes a solid support, a metal-ligand complex tethered to a surface of the solid support through at least two surface reactive moieties of the metal-ligand complex, and a conformationally stable molecular pore defined between the metal-ligand complex and the surface of the solid support. The metal-ligand complex tethered to the surface of the solid support conforms to formula (I):

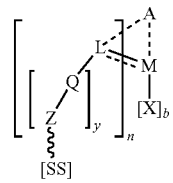

In formula (I), SS represents the solid support as connected through a wavy line to a single molecule of the metal-ligand complex. Thus, the metal-ligand complex represents everything present in formula (I) except for the solid support. The wavy line represents a surface interaction sufficiently strong and stable to hold the position of the metal-ligand complex, particularly a surface reactive group Z of the metal-ligand complex. Examples of surface interactions include but are not limited to covalent bonding, hydrogen bonding, a metal-sulfur bonding, metal-oxygen bonding, metal-nitrogen bonding, pi-stacking, frustrated Lewis pairing, ionic attraction, coulombic bonding, and strong van der Waals interactions. It should be readily understood that the supported catalyst to be used in a catalytic reaction may include multiple metal-ligand complex molecules distributed over the surface of the supported catalyst to a number of molecules per unit area of the surface suitable to establish a desirable catalyst activity in the particular reaction. Example materials for the solid support will be described subsequently.

In formula (I), M represents a catalytic metal center. The catalytic metal center is chosen from transition metals having at least some degree of catalytic activity for a desired reaction. Specific examples of transition metals of the catalytic metal center include, without limitation, chromium, vanadium, magnesium, iron, cobalt, nickel, titanium, zirconium, ruthenium, rhodium, iridium, and palladium. For reactions such as ethylene oligomerization, for example, the catalytic metal center may be iron, chromium, titanium, or zirconium, for example.

As will be understood to those skilled in the art of transition-metal catalysts, the metal-ligand complex of formula (I) has an activated form and a precatalyst form. The form of the metal-ligand complex depends on whether leaving groups X are absent or present. In the activated form of the metal-ligand complex, subscript b is zero, whereby no leaving groups X are present.

In the precatalyst form of the metal-ligand complex, at least one leaving group X is present. The leaving groups X generally hinder or preclude catalytic activity by blocking access of reactant molecules to active sites of the catalytic metal center M. Thus, in the precatalyst form of the metal-ligand complex, subscript b, referring to a number of leaving groups X coordinated to the metal center, may be 1, 2, or 3.

The precatalyst form of the metal-ligand complex may be charged or may be charge-neutral, based on the identities and number of leaving groups X. For example, the subscript b may represent a number of leaving groups that provide charge neutrality to the metal-ligand complex, which would otherwise be charged in the activated form. Alternatively, the subscript b may represent a number of leaving groups that provide an overall charge such as -2, -1, +1 or +2 to the metal-ligand complex, which would otherwise be charged in the activated form. When present, the leaving groups X are independently selected from halogens, monodentate ligands, and bidentate ligands. The monodentate ligands or bidentate ligands may be any chemical moiety that coordinates with or bonds with the metal center in a manner whereby it is readily removable through customary catalyst activation procedures. Further, monodentate ligands or bidentate ligands may be charged or uncharged. Uncharged ligands may coordinate with the metal center through a lone-pair interaction or delta bond, for example, but not affect the overall charge of the metal-ligand complex. Non-limiting examples of leaving groups X include halides, hydrides, acetylacetonates, heterocyclic groups, pyridines, tetrahydrofuran, and pi-coordinated olefins. A non-limiting example of a metal-ligand complex in the precatalyst form that is charge-neutral includes the structure of formula (2A), which is compared to the analogous structure of formula (2B) that has an overall charge of +1.

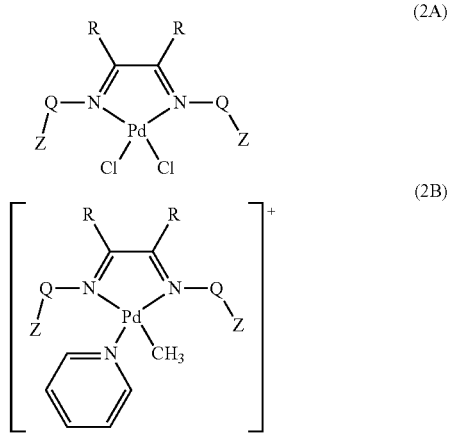

In formula (2A) and formula (2B), Q and Z are as defined in formula (I); and each R is independently —H, $(C_1-C_{40})$ hydrocarbyl, $(C_1-C_{40})$heterohydrocarbyl, —Si$(R^1)_3$, —P$(R^1)_2$, —N$(R^1)_2$, —OR$^1$, —SR$^1$, —NO$_2$, —CN, —CF$_3$, $R^1$S(O)—, $R^1$S(O)$_2$—, $(R^1)_2$C=N—, $R^1$C(O)O—, $R^1$OC(O)—, $R^1$C(O)N$(R^1)$—, $(R^1)_2$NC(O)—, or halogen.

Generally, a maximum number of bonds to the metal center is established by the choice of the transition metal itself and the oxidation state of the transition metal. For most catalytically active transition metals, the maximum number of bonds may be four, five, or six, and the oxidation state of the transition metal may be +2, +3, or +4.

In formula (I), subscript n is 2, 3, or 4, and refers to a number of ligating portions L that are coordinated to the metal-ligand complex. Each L is a ligating portion independently chosen from a monodentate ligating portion coordinated once to the catalytic metal center and a bidentate ligating portion coordinated twice to the catalytic metal center. Accordingly, in formula (I), the dashed bond between the ligating portion L and the catalytic metal center M denotes the instance when a ligating portion is a bidentate ligating portion coordinated twice to the catalytic metal center. Each ligating portion may be any organic structure that coordinates with the catalytic metal center. In some examples, ligating portions may include cyclic structures, bicyclic structures, aromatic structures, heterocyclic structures, or a $C_4-C_{100}$ heterohydrocarbyl. The ligating portions may coordinate with the catalytic metal center through a carbon atom or a heteroatom such as an oxygen atom, a sulfur atom, a nitrogen atom, a phosphorus atom. The ligating portions may coordinate with the catalytic metal center through an eta-bonding mechanism, such as is present when the ligating portion is a cyclopentadiene moiety.

In formula (I), the two, three, or four ligating portions L may be unconnected or may be joined through a connecting portion A. The connecting portion A may be absent from the metal-ligand complex, whereby no two ligating potions are connected except through the catalytic metal center M. When present, the connecting portion A may be any organic moiety covalently bonded to at least two of the ligating portions, for example, to two ligating portions, to three ligating portions, or to four ligating portions. When present, the connecting portion A is optionally coordinated or bonded to the catalytic metal center M. Thus, the connecting portion A may be coordinated or bonded to the catalytic metal center M or the connecting portion A may have no coordination or bond to the catalytic metal center M.

In formula (I), subscript y is 1 or 2 and refers to a number of groups Q—Z bonded to each ligating portion L. Thus, an individual ligating portion L may be attached to a single group Q—Z so as to establish a single tether of the ligating portion to the solid support or to two groups Q—Z so as to establish two tethers of the ligating portion to the solid support. When more than one group Q—Z is connected to a single ligating portion L, the groups Q—Z may be connected to a single atom of the ligating portion or to two unique atoms of the ligating portion.

In formula (I), each Q is a divalent tethering portion independently chosen from $C_6-C_{40}$ hydrocarbylene or $C_6-C_{40}$ heterohydrocarbylene. The $C_6-C_{40}$ hydrocarbylene or $C_6-C_{40}$ heterohydrocarbylene may be substituted or unsubstituted. In some examples, the divalent tethering portions include or are exclusively chemical structures that are rigid and that do not add rotational degrees of freedom to the tethering portion as an extending unit between the ligating portion L and the surface reactive moiety Z at an end of the tethering portion. Examples of rigid chemical structures include neighboring atoms joined by double bonds; methylene linkages, ether linkages, thioether linkages, amide linkages, silyl linkages, amine linkages, monocyclic aromatic structures; polycyclic aromatic structures; phenylene diradicals; diphenylene diradicals; and terphenylene diradicals. In some examples, the divalent tethering portion may be or may include portions such as diradicals of formula (A), formula (B), or formula (C):

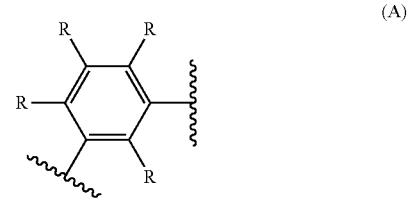

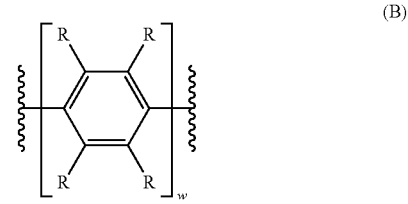

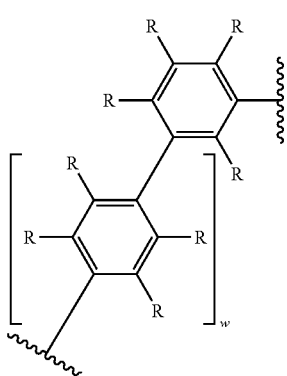

(C)

In formula (A), formula (B), and formula (C), each R is independently —H, $(C_1-C_{40})$hydrocarbyl, $(C_1-C_{40})$heterohydrocarbyl, —Si($R^1$)$_3$, —Si(O$R^1$)($R^1$)$_2$, —Si(O$R^1$)$_2$ ($R^1$), —Si(O$R^1$)$_3$, —P($R^1$)$_2$, —N($R^1$)$_2$, —O$R^1$, —S$R^1$, —NO$_2$, —CN, —CF$_3$, $R^1$S(O)—, $R^1$S(O)$_2$—, ($R^1$)$_2$C=N—, $R^1$C(O)O—, $R^1$OC(O)—, $R^1$C(O)N($R^1$)—, ($R^1$)$_2$NC(O)—, or halogen, where each $R^1$ is independently a $(C_1-C_{30})$ hydrocarbyl, $(C_1-C_{30})$heterohydrocarbyl, or —H. In formula (B) and formula (C), subscript w is an integer from 1 to 10 or from 1 to 5 or from 1 to 3.

In further examples, the divalent tethering portions Q do not include any linear chain portion having greater than five consecutive atoms singly bonded to each other. In further examples, the divalent tethering portions Q do not include any linear chain portion having greater than four consecutive atoms singly bonded to each other that increase degrees of rotational freedom of the tethering portion Q or the combination Q—Z of the tethering portion Q and the surface reactive moiety Z. In further examples, the divalent tethering portions Q do not include any linear chain portion having greater than three consecutive atoms singly bonded to each other that increase degrees of rotational freedom of the tethering portion Q or the combination Q—Z of the tethering portion Q and the surface reactive moiety Z. In further examples, the divalent tethering portions Q do not include any linear chain portion having greater than two consecutive atoms singly bonded to each other that increase degrees of rotational freedom of the tethering portion Q or the combination Q—Z of the tethering portion Q and the surface reactive moiety Z. In the examples of divalent tethering portions, it should be understood that cyclic groups such as phenylene-diyl radicals may be substituted with any number of linear groups, such as linear alkyls, without restriction, because such linear groups do not contribute to degrees of rotational freedom of the tethering portion Q as a whole, or of the combination Q—Z of the tethering portion Q and the surface reactive moiety Z.

In formula (I), each Z is independently a surface reactive moiety tethered to the surface of the solid support by at least one surface interaction between an atom of the surface reactive moiety and the surface. As is implicit in the group Q—Z, each tethering portion Q has a surface reactive moiety Z at a terminal end of the tethering portion Q. The precise identity of the tethering portion Z is selected in view of the material of the solid support SS.

As previously described, the supported catalyst includes a solid support SS. The solid support SS may be any solid material capable of providing surface interactions with the surface reactive moieties Z of the metal-ligand complex. The solid material may be a bulk material, such as a bulk substrate, or particles of the solid material having particle sizes ranging from 1 nanometer to 1 centimeter. The solid support may be selected from ceramics, metals, carbon allotropes.

Examples of ceramics as the solid support include oxides, such as metal oxides and glasses, silica, alumina, silica-alumina, silicates, borosilicates, phosphosilicates, aluminophosphosilicates, and generally any oxide material that includes surface hydroxyl functionalities. When the solid support is a material with surface hydroxyl functionalities, the tethering moiety Z may be a group —SiR$_3$, where each R is alkyl, alkoxy, halide, or —O—, provided at least one group R is —O—. Thereby, the surface interaction of the tethering moiety with the surface of the solid support is a Si—O—Si covalent linkage formed, for example, by a condensation reaction between a halosilane or alkoxysilane with a surface hydroxyl group on the surface of the solid support that holds the position of the tethering moiety Z. In further examples when the solid support is a material with surface hydroxyl functionalities such as silica or alumina, for example, the tethering moiety Z may be a Lewis basic group such as a heterocycle, an amino nitrogen, an ether, an ester, or a nitrile. Thereby, the surface interaction of the tethering moiety with the surface of the solid support is a hydrogen bond or a frustrated Lewis pairing.

Examples of metals as solid supports include any metal capable of forming metal-sulfur bonds upon contact with a thiolate group. Examples of such metals include, without limitation, gold, silver, and copper. When the solid support is a metal capable of forming metal-sulfur bonds, the tethering moiety Z may be a sulfur atom. Thereby, the surface interaction of the tethering moiety with the surface of the solid support is a metal-sulfur bond formed, for example, by a reaction between a thiol, a thioether, or a thioester with a metal atom on the surface of the solid support that holds the position of the tethering moiety Z.

Examples of carbon allotropes as solid supports include, without limitation, graphites, graphenes, carbon nanotubes, and fullerenes. When the solid support is a carbon allotrope, the tethering moiety Z may be a moiety capable of pi-stacking interactions with the surface of the solid substrate. Examples of moieties capable of pi-stacking interactions include moieties with pi-conjugation such as pyrenes, acenes, and triptycenes. Thereby, the surface interaction of the tethering moiety with the surface of the solid support is a pi-stacking interaction that holds the position of the tethering moiety Z.

When the solid support is an oxide material or a metal as previously described, the surface of the solid support optionally may be functionalized or charged to provide a mechanism for establishing or strengthening the surface interaction with the tethering moieties Z. When the solid support is functionalized or charged, the tethering moiety may be an anion or a cation. Examples of anionic and cationic tethering moieties include, without limitation, sulfonates, ammoniums, pyridinium, borates, carboxylates, thiolates, imidazolium, phosphonium, pyrazolium, and ferrocenium. Thereby, the surface interaction of the tethering moiety with the charged surface of the solid support is an ionic or Coulombic interaction or a hydrogen bond that holds the position of the tethering moiety Z.

Non-limiting general structures of some supported catalysts according to formula (I) are provided in FIGS. 1A-3C.

Figure 1B:
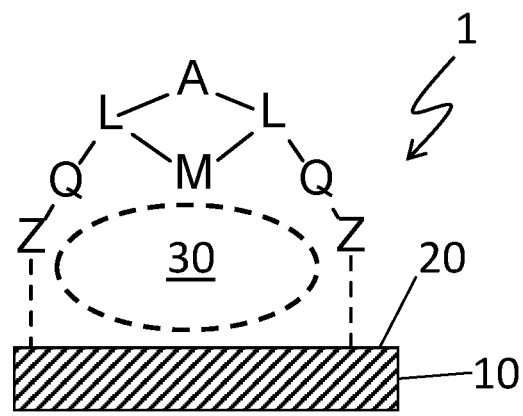
Figure 1C:
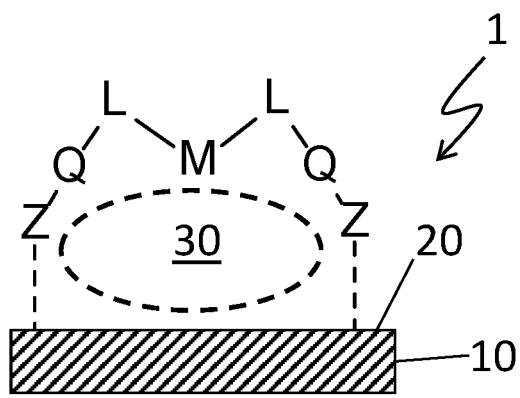

Each of FIGS. 1A-1C shows a supported catalyst 1 including a metal-ligand complex tethered to a surface 20 of a solid support 10, where in formula (I), subscript n is two. A conformationally stable molecular pore 30 is defined between the metal-ligand complex and the surface 20 of the solid support 10. In the supported catalyst 1 of FIG. 1A, a connecting group A is present that is covalently bonded to each of the two ligating portions L and is coordinated with the catalytic metal center M. In the supported catalyst 1 of FIG. 1B, a connecting group A is present that is covalently bonded to each of the two ligating portions L but is not coordinated with the catalytic metal center M. In the supported catalyst 1 of FIG. 1C, a connecting group A is absent.

Figure 2A:
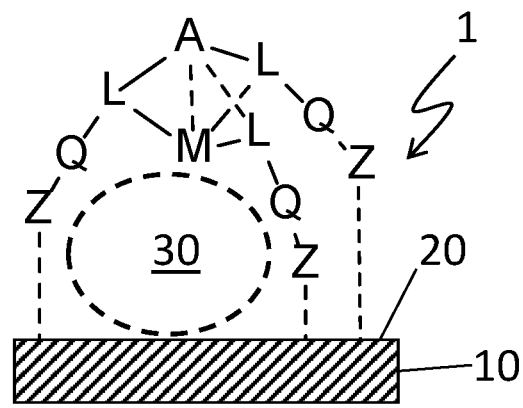
FIGS. 2A-2C are general examples of supported catalysts having three ligating portions, according to embodiments of this disclosure.
Figure 2B:
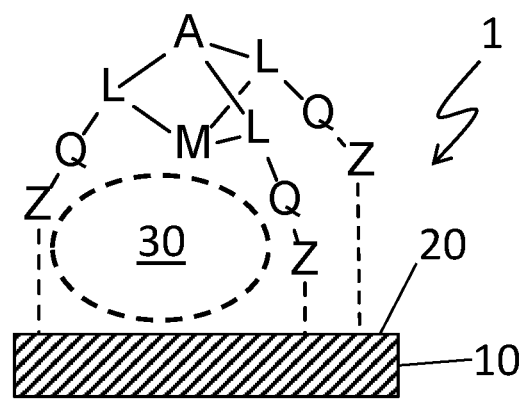
Figure 2C:
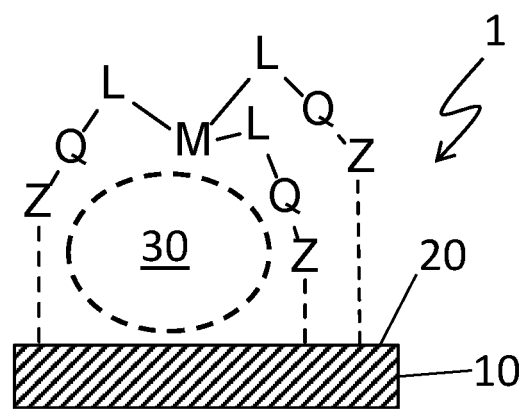

Each of FIGS. 2A-2C shows a supported catalyst 1 including a metal-ligand complex tethered to a surface 20 of a solid support 10, where in formula (I), subscript n is three. A conformationally stable molecular pore 30 is defined between the metal-ligand complex and the surface 20 of the solid support 10. In the supported catalyst 1 of FIG. 2A, a connecting group A is present that is covalently bonded to two of the ligating portions L and is optionally covalently bonded with the third ligating portion L, catalytic metal center M, or both. In the supported catalyst 1 of FIG. 2B, a connecting group A is present that is covalently bonded to all three of the ligating portions L but is not coordinated with the catalytic metal center M. In the supported catalyst 1 of FIG. 2C, a connecting group A is absent.

Figure 3A:
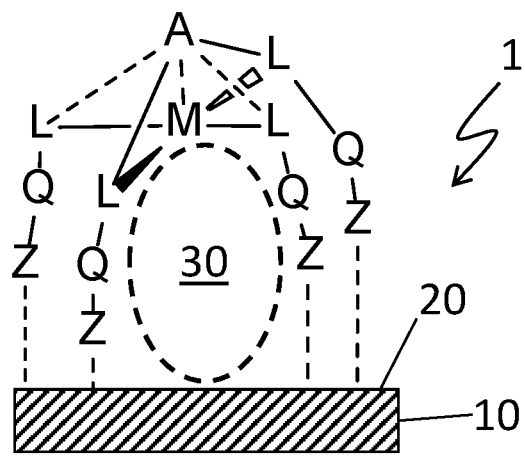
FIGS. 3A-3C are general examples of supported catalysts having four ligating portions, according to embodiments of this disclosure.
Figure 3B:
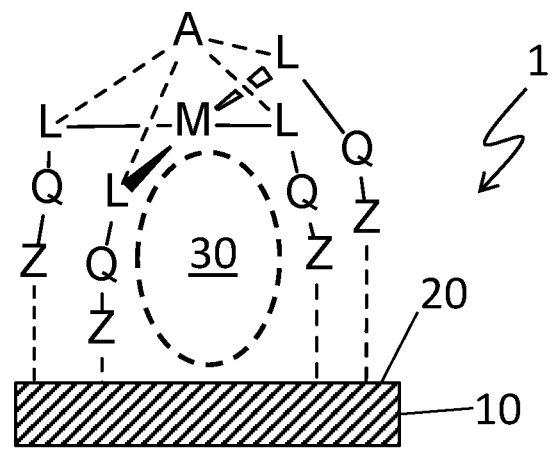
Figure 3C:
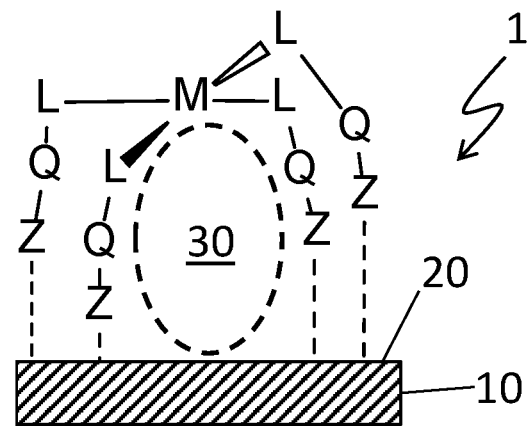

Each of FIGS. 3A-3C shows a supported catalyst 1 including a metal-ligand complex tethered to a surface 20 of a solid support 10, where in formula (I), subscript n is four. A conformationally stable molecular pore 30 is defined between the metal-ligand complex and the surface 20 of the solid support 10. In the supported catalyst 1 of FIG. 3A, a connecting group A is present that is covalently bonded to two of the ligating portions L and is optionally covalently bonded with one or both of the remaining portions L and catalytic metal center M. In the supported catalyst 1 of FIG. 3B, a connecting group A is present that is covalently bonded to any two of the ligating portions L but is not coordinated with the catalytic metal center M. In the supported catalyst 1 of FIG. 3C, a connecting group A is absent.

Table 1 provides structures (1)-(14) as specific non-limiting examples of metal-ligand complex portions of the supported catalyst of formula (I). In the structures (1)-(14), each M, A, Q, and Z are as defined in formula (I); N is a nitrogen atom; S is a sulfur atom; P is a phosphorus atom; and each R is independently —H, $(C_1-C_{40})$hydrocarbyl, $(C_1-C_{40})$heterohydrocarbyl, —Si$(R^1)_3$, —P$(R^1)_2$, —N$(R^1)_2$, —OR$^1$, —SR$^1$, —NO$_2$, —CN, —CF$_3$, $R^1$S(O)—, $R^1$S(O)$_2$—, $(R^1)_2$C=N—, $R^1$C(O)O—, $R^1$OC(O)—, $R^1$C(O)N$(R^1)$—, $(R^1)_2$NC(O)—, or halogen, where each $R^1$ is independently a $(C_1-C_{30})$hydrocarbyl, $(C_1-C_{30})$heterohydrocarbyl, or —H. For the sake of conciseness, the structures in Table 1 are provided in the active form, without any leaving groups X.

TABLE 1

| Structure | Metal-Ligand Complex | Formula (1) Subscript n | Formula (1) Subscript y |
|---|---|---|---|
| (1) | | 2 | 1 |
| (2) | | 2 | 1 |
| (3) | | 2 | 1 |
| (4) | | 2 | 1 |

TABLE 1-continued

| Structure | Metal-Ligand Complex | Formula (1) Subscript n | Formula (1) Subscript y |
|---|---|---|---|
| (5) | | 2 | 1 |
| (6) | | 2 | 1 |
| (7) | | 2 | 1 |
| (8) | | 2 | 2 |
| (9) | | 2 | 1 |
| (10) | | 2 | 1 |

TABLE 1-continued

| Structure | Metal-Ligand Complex | Formula (1) Subscript n | Formula (1) Subscript y |
|---|---|---|---|
| (11) | [structure: bis-imidazole bridged metal complex with R groups, N—M—N coordination, Q—Z tethers] | 2 | 1 |
| (12) | [structure: tris(pyridine) metal complex with R groups and Q—Z tether, subscript 3] | 3 | 1 |
| (13) | [structure: phenolate-methylamine metal complex with R groups and Q—Z tether, subscript 3] | 3 | 1 |
| (14) | [structure: tetrakis(pyridine) metal complex with R groups and Q—Z tether, subscript 4] | 4 | 1 |

Figure 4A:
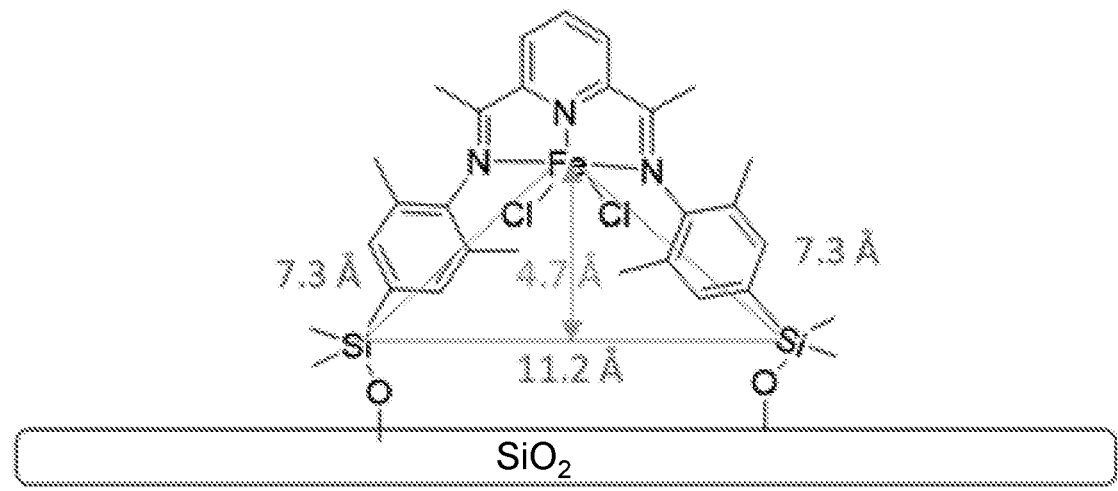
FIG. 4A is a diagram of pore dimensions resulting from an exemplary metal-ligand complex having tethering portions based on phenylene-1,4-diyl groups and being tethered to a solid support through a Si—O—Si linkage.
Figure 4B:
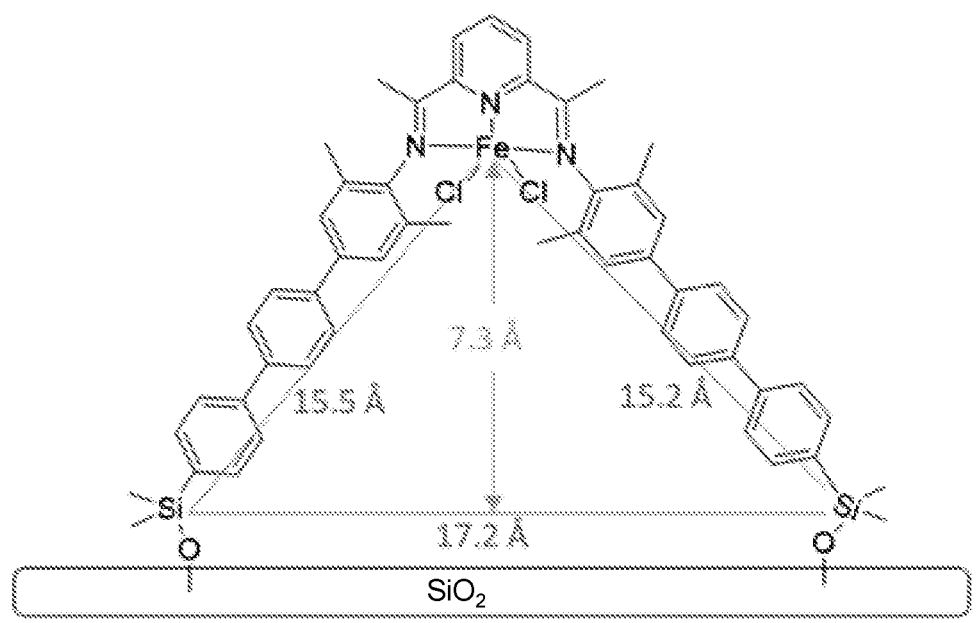
FIG. 4B is a diagram of pore dimensions resulting from an exemplary metal-ligand complex having tethering portions based on terphenylene-1,4"-diyl groups and being tethered to a solid support through a Si—O—Si linkage.

Owing to the structure of the metal-ligand complex, the supported catalyst includes a conformationally stable molecular pore defined between the metal-ligand complex and the surface of the solid support. Conformational stability of the molecular pore results from a combination of the chemical rigidity of the tethering portions Q and the type and number of surface interactions between the surface of the solid support and the surface reactive moieties. FIGS. 4A and 4B are illustrative examples of a supported catalyst and the conformationally stable molecular pore of the supported catalyst.

The supported catalyst of FIG. 4A includes an iron metal center in the precatalyst form with two coordinated chloro leaving groups, two nitrogen atoms as litgating portions, and a heterocyclic connecting group having a nitrogen atom coordinated to the metal center. The supported catalyst of FIG. 4A further includes two tethering portions, both 2,6-dimethylphenylene-1,4-diyl, respectively bonded to the ligating portions. Each tethering portion terminates with a SiO— surface reactive moiety derived from a condensation reaction of a dimethylmethoxysilyl group added to the end of the tethering portion with surface hydroxyl groups of the $SiO_2$ solid support. Accordingly, the surface interaction between the metal-ligand complex and the solid support is a covalent Si—O—Si linkage. Owing to the chemical rigidity of the tethering portions, combined with the fixed covalent surface interaction of the siloxyl group with the solid support, the effective dimensions of the molecular pore are quantifiable, well-defined, and substantially constant. In particular, the two silicon atoms are separated by about 11.2 angstroms, which approximates a width of the molecular pore. A distance from a line connecting the two silicon atoms and the iron metal center is approximately 4.7 angstroms, which approximates a height of the molecular pore. The volume of the molecular pore is further quantified in view of the distance between the silicon atoms and the iron metal center being about 7.3 angstroms in each case for the symmetrical example, and the constant angle defined by the three atoms Si—Fe—Si. The angle defined by the three atoms Si—Fe—Si is fixed, owing to the structure of the ligating portion and the connecting portion, the combination of which is the tridentate ligand coordinated to the metal center. The molecular pore is further described in that the two chloro leaving groups, which represent the location of active sites in the activated form of the metal-ligand complex, are oriented toward the solid support. Thereby, in a catalytic reaction, the reactant can enter into the conformationally stable molecular pore and be exposed to the active sites of the metal center.

It should be readily apparent that the dimensions and environment of the molecular pore may be tailored through specific choices of the ligating portion and the tethering portions. In comparison with the supported catalyst of FIG. 4A with 2,6-dimethylphenylene-1,4-diyl tethering portions, in the supported catalyst of FIG. 4B, the tethering portions are based on para-terphenylene-1,4"-diyl groups having three aromatic rings instead of one. Thereby, the effective width of the molecular pore is increased from about 11.2 angstroms to about 17.2 angstroms and the effective height of the molecular pore is increased from about 4.7 angstroms to about 7.3 angstroms. Accordingly, the supported catalyst of FIG. 4B may be better suited for catalytic reactions involving larger molecules or monomers than the molecules or monomers best suited for the supported catalyst of FIG. 4A.

It should be understood that an increase in the effective height of the molecular pore lessens the potential influence of the solid support in the catalytic reactions, particularly any interaction between the active site of the metal center and the surface of the solid support. Therefore, the dimensions of the molecular pore may be tailored such that the effective height is sufficiently great to accommodate any reactant molecules or monomers while not being so overly great to eliminate any influence of the solid support on the reactions. Without intent to be bound by theory, it is believed that the solid support as a boundary of the molecular pore may provide a pre-concentration effect on the reactants of a catalytic reaction, thereby bringing a higher concentration of reactants in the proximity of the active site than would be expected with a homogeneous catalyst. The pre-concentration effect, in turn, may beneficially influence reaction binding kinetics or catalyst activity. On the other hand, if the active site of the metal center is overly distant from the solid support, any benefit associated with the solid support as a source or pre-concentration may be diminished.

The conformational stability of the molecular pore may be further expressed quantitatively in view of any possible molecular rotations or shifting through the metal-ligand complex in a manner that change the effective width, the effective height, or the overall volume of the molecular pore. For example, the molecular pore may be conformationally stable such that while the metal-ligand complex is tethered to the solid support during a catalytic reaction, the distance between the catalytic metal center M and the solid support never deviates by greater than 20%, greater than 10%, greater than 5%, greater than 1%, greater than 0.5%, or greater than 0.1% from an average distance measured over a period of time such as one minute. Similarly, the molecular pore may be conformationally stable such that while the metal-ligand complex is tethered to the solid support during a catalytic reaction, the total volume of the molecular pore never deviates by greater than 20%, greater than 10%, greater than 5%, greater than 1%, greater than 0.5%, or greater than 0.1% from an average distance measured over a period of time such as one minute.

Without intent to be bound by theory, it is believed that the supported catalysts of this disclosure with a conformationally stable molecular pore may be tailored to more finely discriminate between sizes of reactants or products. For example, in ethylene oligomerization where small-length oligomers are the desired product, the molecular pore may be tailored to shift the product distribution to avoid production of overly large oligomers or polymers. The molecular pore may also affect the linear vs. branching of the ethylene oligomers relative to a homogeneous catalyst that is not tethered and facing a surface. For a catalyst that operates on crude oil, sulfur-containing asphaltenes may poison a conventional homogeneous catalyst, but such large molecules would be precluded from interacting with the supported catalysts described herein having the conformationally stable molecular pore.

EXAMPLES

The following Examples are offered by way of illustration and are presented in a manner such that one skilled in the art should recognize are not meant to be limiting to the present disclosure as a whole or to the appended claims.

Example 1

Attachment of Metal-Ligand Complex to Solid Support

Figure 5:
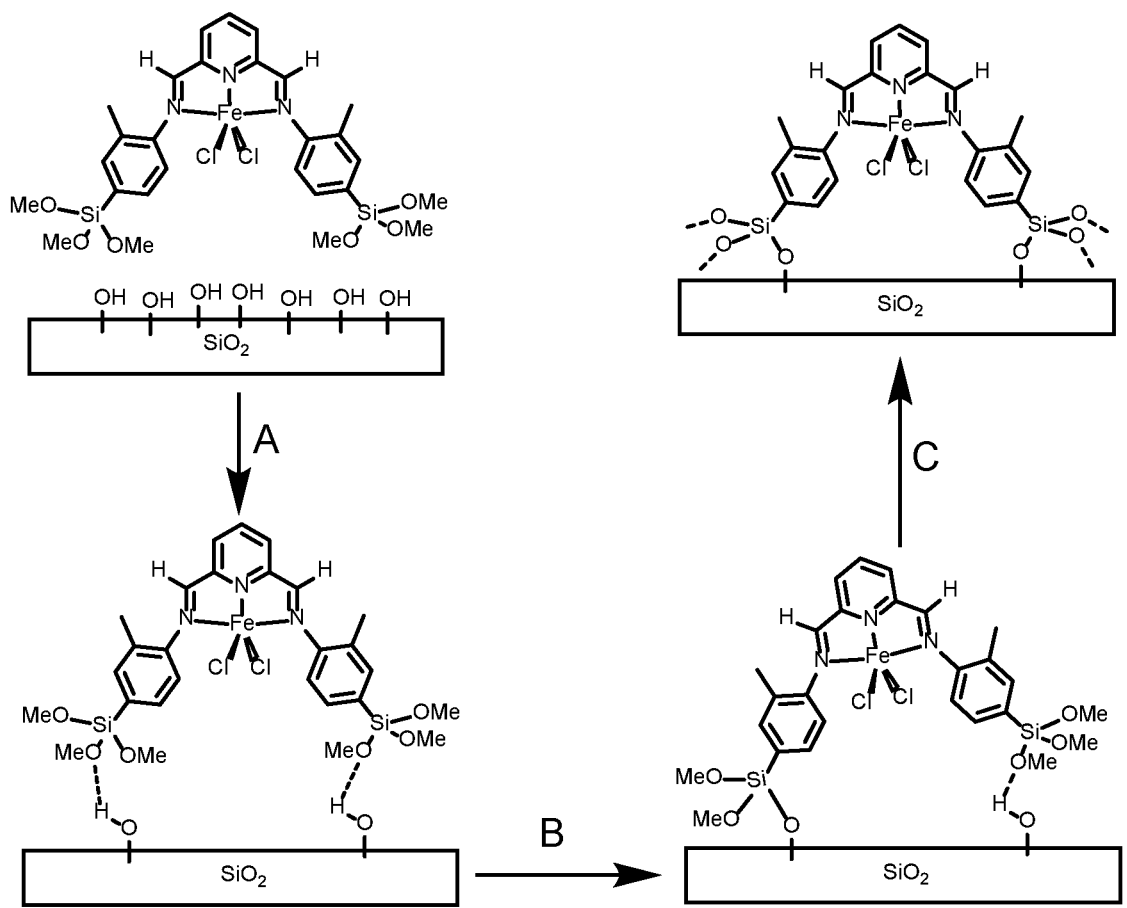
FIG. 5 is an example reaction scheme for supporting a metal-ligand complex on a solid support to form a supported catalyst according to embodiments of this disclosure.

Referring to FIG. 5, in this Example 1, a supported catalyst according to formula (I) as previously described is prepared. The metal-ligand complex of the supported catalyst is an iron catalytic metal center complexed with a tridentate pyridyldiimine ligand including 2-methylphenylene-1,4-diyl tethering portions and methoxysilyl surface reactive moieties. The solid support is a silica gel.

Because the metal-ligand complex includes more than one trialkoysilyl group, the procedure for attaching the metal-ligand complex is adjusted to prevent catalyst-catalyst bimolecular condensation reactions. Such bimolecular condensation reactions may cause catalyst molecules to cluster on the surface or to form oligomeric catalysts incapable of direct surface interactions. The procedure is adaptable using a variety of solvents and conditions. In the present example, the tethering procedure is conducted in two phases. In a first phase, a pre-association step, the metal-ligand complexes are distributed evenly on the surface, and intermolecular bicomplex reactions are minimized. In a second phase, a surface-reaction step, the metal-ligand complexes are fixed exclusively to the surface of the solid support and not to other complexes. Some criteria for the reaction conditions include: (a) none of the solvents contain O—H bonds that can react with the alkoxysilane groups; (b) the initial solvent has good dissolving power of the metal complex starting material, but is not so polar as to facilitate premature formation of Si—O—Si linkages that may result in less uniform functionalization of the silica surface or formation of oligomers of the metal complex); (c) the solvent for the heated portion of the reaction is sufficiently polar to facilitate the condensation reaction and is capable of being heated above 50° C.; and (d) to prevent bimolecular condensations, the metal complex precursor solution should be relatively dilute and excess metal complex should be rinsed away.

To remove surface-bound water and control the density of surface silanol groups, the silica (Aerosil 200, Evonik) is heated under vacuum and brought into an inert-atmosphere glovebox. A slurry is formed with 500 mg of silica gel powder and 15 mL of anhydrous dichloromethane in a 20-mL scintillation vial. The bis(trimethoxysilyl) iron complex (80 mg) is dissolved in 2 mL dichloromethane and added to the silica slurry (reaction A of FIG. 5). After 5 minutes, this slurry is filtered and washed with dichloromethane to remove any complexes that are not strongly interacting with the silica gel. At this step, in the filter cake, the iron complexes may be attached to the silica only via weak hydrogen bonds.

To promote the formation of new Si-O bonds, the filter cake is resuspended in 15 mL tetrahydrofuran, and stirred at 60° C. for 16 hours (reaction B of FIG. 5).

Then the reaction is cooled and filtered, the filter cake is washed with tetrahydrofuran, dichloromethane, and hexanes and dried under vacuum to isolate 400 milligrams of light green powder (reaction C of FIG. 5). The combined filtrates are concentrated under vacuum to 66 milligrams of mass. With approximately 14 mg of complex (18.3 μmol in 400 mg of product, the supported catalyst has about 1.02 milligrams of iron per 400 milligrams of product.

Example 2

Ethylene Oligomerization Reactions

To assess the characteristics of supported catalysts of the present disclosure, two metal-ligand complexes (Catalyst B and Catalyst D) were prepared and supported on silica gel as described in Example 1 and were tested as heterogeneous catalysts for ethylene oligomerization reaction. As comparative examples, untethered metal-ligand complexes (Catalyst A and Catalyst C) were tested as homogenous catalysts for the same ethylene oligomerization reaction. Table 2 provides the catalysts tested.

TABLE 2

| Catalyst A (Comparative) | |
|---|---|
| Catalyst B | |

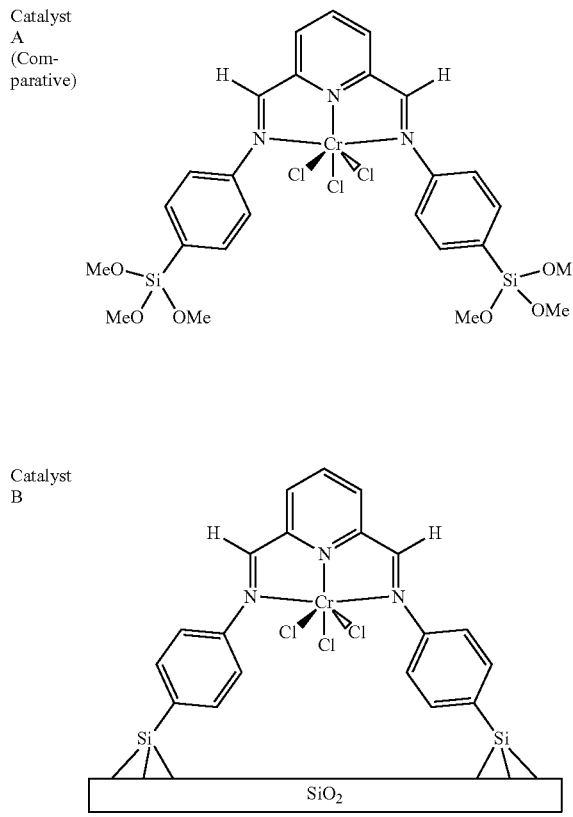

TABLE 2-continued

| Catalyst C (Comparative) | |
|---|---|
| Catalyst D | |

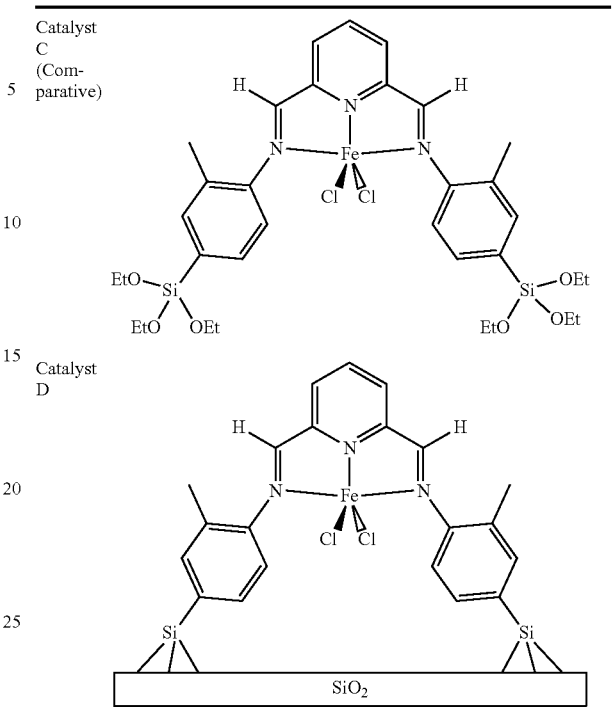

In each reaction, a 100-mL stainless steel reactor equipped with an overhead stirrer, internal thermocouple, and a glass liner was weighed, heated to 160° C., and placed under 100 alternating cycles of vacuum followed by 5 atm nitrogen. The reactor was then allowed to cool to 45° C. Two compatible stainless-steel chargers (Charger A and Charger B) were oven-dried and brought into an inert-atmosphere glovebox.

Charger A was loaded with anhydrous methylcyclohexane (44.8 g) and modified methylaluminoxane MMAO-3A (154.2 mg of 7 wt% Al solution in heptane purchased from Nouryon, or 400 μmol Al). A solution or slurry of the catalyst (0.8 μmol transition metal) in chlorobenzene (400 μL) was transferred to Charger B. The chargers were sealed, brought out of the glovebox, and attached to the reactor under nitrogen counterflow. The contents of Charger A were transferred to the reactor using 3 bar of nitrogen backing pressure. The stirrer was set to 300 rpm, and the reactor temperature was equilibrated to 45° C. Then the contents of Charger B were transferred to the reactor using 6 bar of nitrogen backing pressure, and the stirrer speed was increased to 1500 rpm. The reactor was pressurized with high purity ethylene to 45 bar of total pressure, and ethylene dosing to maintain this pressure was initiated. After 60 minutes at 45 bar, the ethylene feed was shut off, and the reactor heating jacket was removed. The stirrers were set to 300 rpm, and the reactors were cooled in an ice bath. Once the reactor reached 10° C., its pressure was vented, and methanol was added to quench the reaction. After 15 minutes, stirrer was turned off, the reactor exterior was dried, and the combined mass of the reactor and its contents was recorded to calculate total product mass.

The composition of the liquids in the product mixture was determined via GC-FID, while the solids were isolated via filtration to calculate polymer byproduct mass. The data from these experiments is provided in Table 3.

TABLE 3

| Catalyst | Activity | Polymer (mg) | Weight Percent Linear Alpha Olefin by Carbon Number Based on Total Weight of Linear Alpha Olefins | | | | | | | | |
|---|---|---|---|---|---|---|---|---|---|---|---|
| | | | C4 | C6 | C8 | C10 | C12 | C14 | C16 | C18 | C20 |
| Catalyst A (Comparative) | 23766 | 62.2 | 72.3 | 14.9 | 7.2 | 1.1 | 1.0 | 1.0 | 0.8 | 0.4 | 0.5 |
| Catalyst B | 22838 | 1.9 | 84.7 | 8.3 | 4.3 | 0.8 | 0.8 | 0.4 | 0.7 | 0.0 | 0.0 |
| Catalyst C (Comparative) | 83800 | 449.6 | 19.1 | 24.1 | 16.5 | 11.2 | 7.9 | 5.7 | 4.2 | 3.1 | 2.3 |
| Catalyst D | 23520 | 19.1 | 22.3 | 23.2 | 15.5 | 10.0 | 7.1 | 5.2 | 4.0 | 3.1 | 2.3 |

From the data in Table 3, Catalyst A and Catalyst B are directly comparable, as are Catalyst C and Catalyst D. Both pairs show notable differences. In particular, the supported catalyst B and D produced substantially less polymer (1.9 mg and 19.1 mg, respectively) than their unsupported analogs catalysts A and C (62.2 mg and 449.6 mg, respectively). Also, the linear alpha-olefin product amounts were shifted to lighter oligomers with lower carbon numbers from the supported catalysts, with greater amounts of ethylene dimers (C4) for the supported catalysts in each instance. Thus, the supported catalysts as described herein are expected to provide a benefit of less undesirable polymer formation in ethylene oligomerization reactions for which short-length ethylene oligomers are the desired product. Polyethylene byproduct is especially deleterious in industrial practice, as it will foul the reactor and downstream heat exchangers, resulting in greater downtime of the ethylene oligomerization unit.

Item Listing

Item 1: A supported catalyst comprising: a solid support; and a metal-ligand complex tethered to a surface of the solid support through at least two surface reactive moieties of the metal-ligand complex; and a conformationally stable molecular pore defined between the metal-ligand complex and the surface of the solid support, wherein the metal-ligand complex tethered to the surface of the solid support has formula (I):

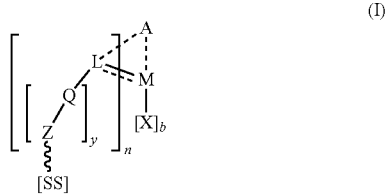

(I)

Where, in formula (I): SS is the solid support; M is a catalytic metal center chosen from transition metals; the metal-ligand complex has an activated form and a precatalyst form; b is 0 in the activated form of the metal-ligand complex; b is 1, 2, or 3 in the precatalyst form of the metal-ligand complex, wherein each X is a leaving group chosen from halogens, monodentate ligands, and bidentate ligands; n is 2, 3, or 4; each L is a ligating portion independently chosen from a monodentate ligating portion coordinated once to the catalytic metal center and a bidentate ligating portion coordinated twice to the catalytic metal center; A is absent or is a connecting portion that is covalently bonded to at least two of the ligating portions L and optionally is coordinated to the catalytic metal center M; y is 1 or 2; each Q is a divalent tethering portion independently chosen from $C_6$—$C_{40}$ hydrocarbylene or $C_6$—$C_{40}$ heterohydrocarbylene, wherein the $C_6$—$C_{40}$ hydrocarbylene or $C_6$—$C_{40}$ heterohydrocarbylene is substituted or unsubstituted; each Z is independently a surface reactive moiety tethered to the surface of the solid support by at least one surface interaction between an atom of the surface reactive moiety and the surface; and Q—Z taken together does not include any linear chain portion having greater than four consecutive atoms each singly bonded to each other.

Item 2: The supported catalyst of Item 1, wherein the divalent tethering portions Q consist of rigid chemical structures selected from the group consisting of neighboring atoms joined by double bonds; methylene linkages, ether linkages, thioether linkages, amide linkages, silyl linkages, amine linkages, monocyclic aromatic structures; polycyclic aromatic structures; phenylene diradicals; diphenylene diradicals; and terphenylene diradicals, wherein any of the rigid chemical structures are optionally substituted.

Item 3: The supported catalyst of any one of Items 1 to 2, wherein the divalent tethering portions Q do not include any linear chain portion having greater than three consecutive atoms singly bonded to each other.

Item 4: The supported catalyst of any one of Items 1 to 3, wherein active sites of the activated form of the metal-ligand complex are oriented toward the surface of the solid support.

Item 5: The supported catalyst of any one of Items 1 to 4, wherein the surface interaction is chosen from covalent bonding, hydrogen bonding, Lewis interaction, metal-sulfur bonding, pi-stacking, Coulombic interaction, and van der Waals interaction.

Item 6: The supported catalyst of any one of Items 1 to 5, wherein the divalent tethering portions Q are chosen from formula (A), formula (B), or formula (C):

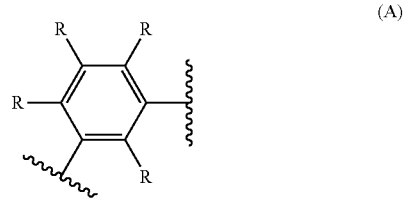

(A)

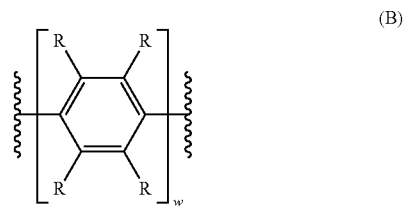

(B)

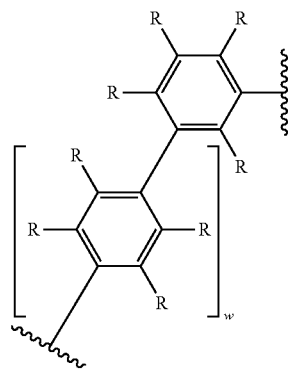

(C)

Where, in each of formula (A), formula (B), and formula (C), each R is independently —H, $(C_1-C_{40})$hydrocarbyl, $(C_1-C_{40})$heterohydrocarbyl, —Si$(R^1)_3$, —Si$(OR^1)(R^1)_2$, —Si$(OR^1)_2(R^1)$, —Si$(OR^1)_3$, —P$(R^1)_2$, —N$(R^1)_2$, —OR$^1$, —SR$^1$, —NO$_2$, —CN, —CF$_3$, $R^1$S(O)$_2$—, $(R^1)_2$C=N—, $R^1$C(O)O—, $R^1$OC(O)—, $R^1$C(O)N$(R^1)$—, $(R^1)_2$NC(O)—, or halogen, where each $R^1$ is independently a $(C_1-C_{30})$ hydrocarbyl, $(C_1-C_{30})$heterohydrocarbyl, or —H; and w is 1, 2, or 3.

Item 7: The supported catalyst of any one of Items 1 to 6, wherein the metal-ligand complex has a structure according to any of formulas (1)-(13):

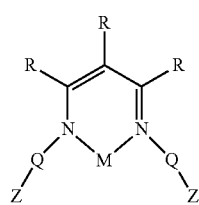

(1)

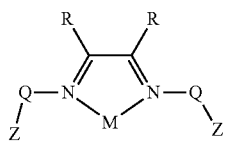

(2)

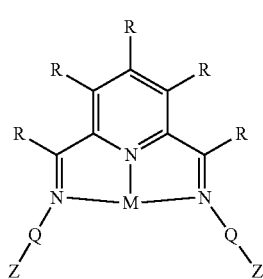

(3)

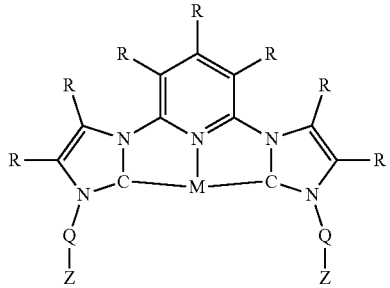

(4)

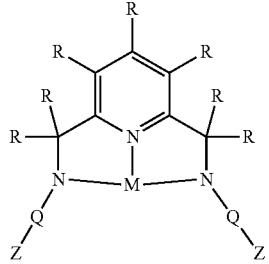

(5)

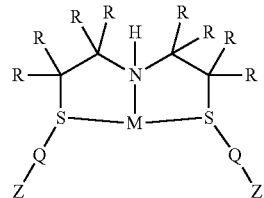

(6)

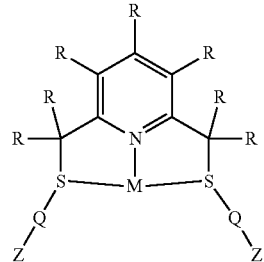

(7)

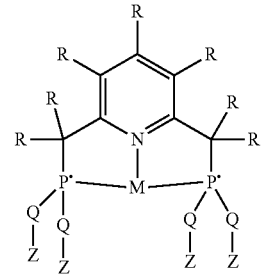

(8)

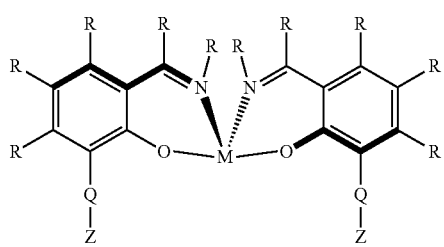

(9)

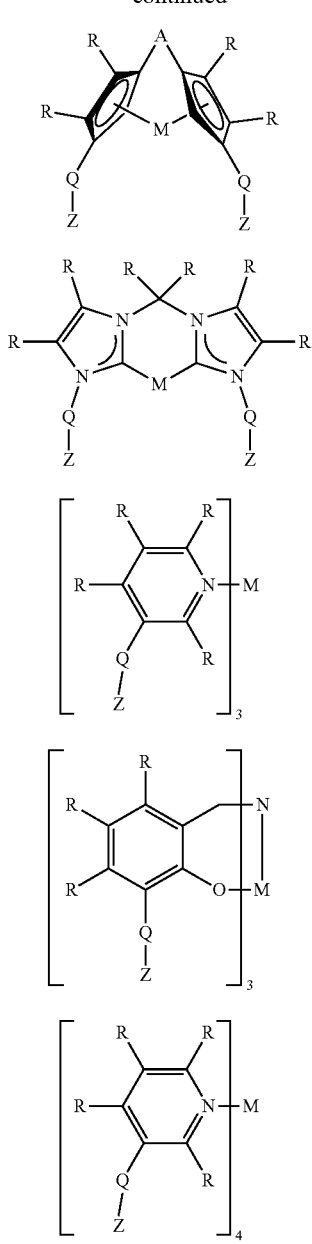

Where, in each of formulas (1)-(13): each M, A, Q, and Z are as defined in formula (I); and each R is independently —H, $(C_1$—$C_{40})$hydrocarbyl, $(C_1$—$C_{40})$heterohydrocarbyl, —Si$(R^1)_3$, —P$(R^1)_2$, —N$(R^1)_2$, —O$R^1$, —S$R^1$, —NO$_2$, —CN, —CF$_3$, $R^1$S(O)—, $R^1$S(O)$_2$—, $(R^1)_2$C=N—, $R^1$C(O)O—, $R^1$OC(O)—, $R^1$C(O)N($R^1$)—, $(R^1)_2$NC(O)—, or halogen, where each $R^1$ is independently a $(C_1$—$C_{30})$hydrocarbyl, $(C_1$—$C_{30})$heterohydrocarbyl, or —H.

Item 8: The supported catalyst of any one of Items 1 to 7, wherein the catalytic metal center is selected from the group consisting of chromium, vanadium, magnesium, iron, cobalt, nickel, titanium, zirconium, ruthenium, rhodium, iridium, and palladium.

Item 9: The supported catalyst of any one of Items 1 to 8, wherein b is 1, 2, or 3, and each leaving group X is selected from the group consisting of halogens, amines, and amides.

Item 10: The supported catalyst of any one of Items 1 to 9, wherein each ligating portion comprises at least one atom coordinated with the catalytic metal center, the at least one atom chosen from carbon, nitrogen, sulfur, oxygen, or phosphorus.

Item 11: The supported catalyst of any one of Items 1 to 10, wherein the solid support is chosen from metal oxides, glasses, metals, planar carbon allotropes, and metals or ceramics having charged surfaces.

Item 12: The supported catalyst of any one of Items 1 to 11, wherein the solid support is silica, alumina, or a silica-alumina.

Item 13: The supported catalyst of any one of Items 1 to 12, wherein the solid support is silica and the surface reactive moiety is tethered to the surface through a Si—O—Si linkage.

Item 14: The supported catalyst of any one of Items 1 to 11, wherein the solid support is a metal and the surface reactive moiety comprises a thiol, a thioether, or a thioester.

Item 15: The supported catalyst of any one of Items 1 to 11, wherein the solid support is graphite, graphene, carbon nanotubes, or a fullerene and the surface reactive moiety comprises a pyrenyl, an acenyl, or a triptycenyl.

Item 16: The supported catalyst of any one of Items 1 to 15, wherein the surface of the solid support is charged and the surface reactive moiety comprises a sulfonate, an ammonium, a pyridinium, a borate, a carboxylate, a thiolate, an imidazolium, a phosphonium, a pyrazolium, or a ferrocenium.

Item 17: A method for oligomerizing ethylene, the method comprising contacting ethylene in a reactor with a supported catalyst according to any one of Items 1 to 16.

Item 18: Use of a supported catalyst according to any one of Items 1 to 17 as a catalyst for olefin hydrogenation, epoxidation, hydroformylation, dimerization, trimerization, oligomerization, or polymerization.

Item 19: Use of a supported catalyst according to any one of Items 1 to 17 as a catalyst for ethylene dimerization, ethylene trimerization, ethylene oligomerization, or ethylene polymerization.

It is noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue. The term "substantially" is used herein also to represent the degree by which a quantitative representation may vary from a stated reference without resulting in a change in the basic function of the subject matter at issue. Thus, it is used to represent the inherent degree of uncertainty that may be attributed to any quantitative comparison, value, measurement, or other representation, referring to an arrangement of elements or features that, while in theory would be expected to exhibit exact correspondence or behavior, may in practice embody something less than exact.

Unless otherwise defined, all technical and scientific terms used herein have the same meaning as commonly understood by one of ordinary skill in the art to which the invention belongs. The terminology used in the description herein is for describing particular embodiments only and is not intended to be limiting. As used in the specification and appended claims, the singular forms "a," "an," and "the" are intended to include the plural forms as well, unless the context clearly indicates otherwise.

It is noted that one or more of the following claims utilize the term "wherein" as a transitional phrase. For the purposes of defining the present technology, it is noted that this term is introduced in the claims as an open-ended transitional phrase that is used to introduce a recitation of a series of characteristics of the structure and should be interpreted in like manner as the more commonly used open-ended preamble term "comprising."

It should be understood that where a first component is described as "comprising" or "including" a second component, it is contemplated that, in some embodiments, the first component "consists" or "consists essentially of" the second component. Additionally, the term "consisting essentially of" is used in this disclosure to refer to quantitative values that do not materially affect the basic and novel characteristic(s) of the disclosure.

It should be understood that any two quantitative values assigned to a property or measurement may constitute a range of that property or measurement, and all combinations of ranges formed from all stated quantitative values of a given property or measurement are contemplated in this disclosure.

While particular embodiments have been illustrated and described herein, it should be understood that various other changes and modifications may be made without departing from scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. A supported catalyst comprising:
   a solid support; and
   a metal-ligand complex tethered to a surface of the solid support through at least two surface reactive moieties of the metal-ligand complex; and
   a conformationally stable molecular pore defined between the metal-ligand complex and the surface of the solid support, wherein the metal-ligand complex tethered to the surface of the solid support has formula (I):

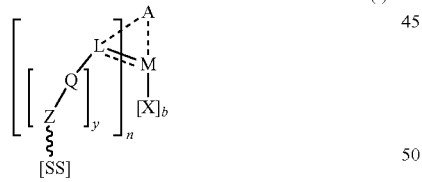

where:
   SS is the solid support;
   M is a catalytic metal center chosen from transition metals;
   the metal-ligand complex has an activated form and a precatalyst form;
   b is 0 in the activated form of the metal-ligand complex;
   b is 1, 2, or 3 in the precatalyst form of the metal-ligand complex, wherein each X is a leaving group chosen from halogens, monodentate ligands, and bidentate ligands;
   n is 2, 3, or 4;
   each L is a ligating portion independently chosen from a monodentate ligating portion coordinated once to the catalytic metal center and a bidentate ligating portion coordinated twice to the catalytic metal center;
   A is absent or is a connecting portion that is covalently bonded to at least two of the ligating portions L and optionally is coordinated to the catalytic metal center M;
   y is 1 or 2;
   each Q is a divalent tethering portion independently chosen from $C_6$—$C_{40}$ hydrocarbylene or $C_6$—$C_{40}$ heterohydrocarbylene, wherein the $C_6$—$C_{40}$ hydrocarbylene or $C_6$—$C_{40}$ heterohydrocarbylene is substituted or unsubstituted;
   each Z is independently a surface reactive moiety tethered to the surface of the solid support by at least one surface interaction between an atom of the surface reactive moiety and the surface; and
   Q—Z taken together does not include any linear chain portion having greater than four consecutive atoms each singly bonded to each other.

2. The supported catalyst of claim 1, wherein the divalent tethering portions Q consist of rigid chemical structures selected from the group consisting of neighboring atoms joined by double bonds; methylene linkages, ether linkages, thioether linkages, amide linkages, silyl linkages, amine linkages, monocyclic aromatic structures; polycyclic aromatic structures; phenylene diradicals; diphenylene diradicals; and terphenylene diradicals, wherein any of the rigid chemical structures are optionally substituted.

3. The supported catalyst of claim 1, wherein the divalent tethering portions Q do not include any linear chain portion having greater than three consecutive atoms singly bonded to each other.

4. The supported catalyst of claim 1, wherein active sites of the activated form of the metal-ligand complex are oriented toward the surface of the solid support.

5. The supported catalyst of claim 1, wherein the surface interaction is chosen from covalent bonding, hydrogen bonding, Lewis interaction, metal-sulfur bonding, pi-stacking, Coulombic interaction, and van der Waals interaction.

6. The supported catalyst of claim 1, wherein the divalent tethering portions Q are chosen from formula (A), formula (B), or formula (C):

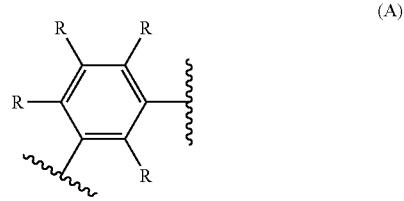

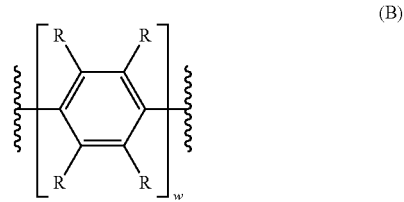

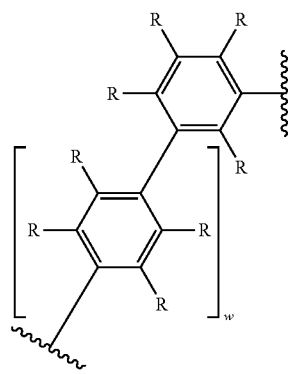
(C)

where, in each of formula (A), formula (B), and formula (C), each R is independently —H, $(C_1-C_{40})$hydrocarbyl, $(C_1-C_{40})$heterohydrocarbyl, —Si$(R^1)_3$, —Si$(OR^1)(R^1)_2$, —Si$(OR^1)_2(R^1)$, —Si$(OR^1)_3$, —P$(R^1)_2$, —N$(R^1)_2$, —OR$^1$, —SR$^1$, —NO$_2$, —CN, —CF$_3$, R$^1$S(O)—, R$^1$S(O)$_2$—, R($^1$)$_2$C=N—, R$^1$C(O)O—, R$^1$OC(O)—, R$^1$C(O)N(R$^1$)—, $(R^1)_2$NC(O)—, or halogen, where each R$^1$ is independently a $(C_1-C_{30})$hydrocarbyl, $(C_1-C_{30})$heterohydrocarbyl, or —H; and w is 1, 2, or 3.

7. The supported catalyst of claim 1, wherein the metal-ligand complex has a structure according to any of formulas (1)-(13):

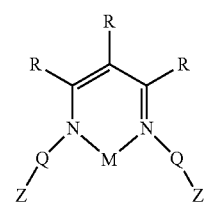
(1)

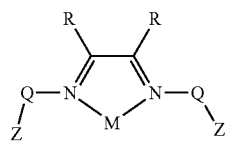
(2)

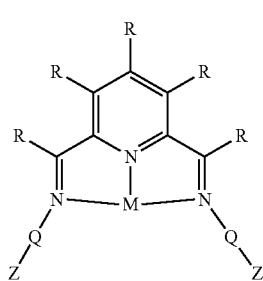
(3)

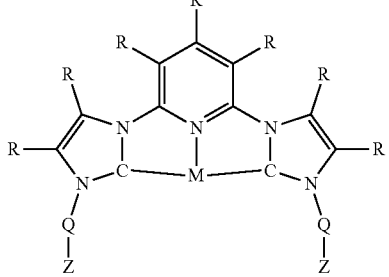
(4)

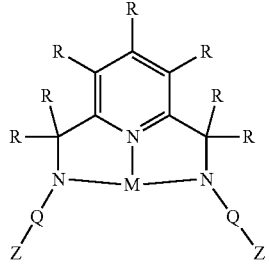
(5)

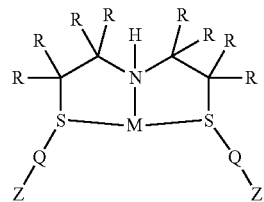
(6)

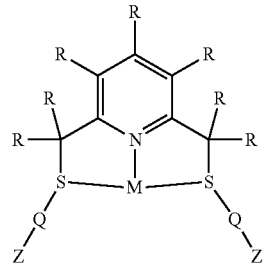
(7)

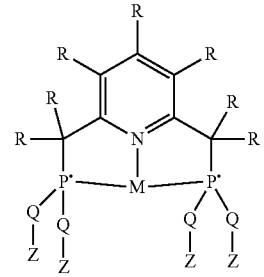
(8)

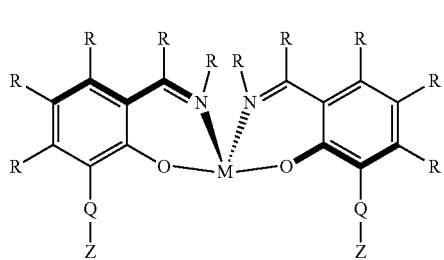
(9)

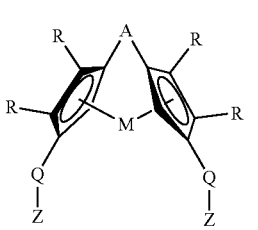
(10)

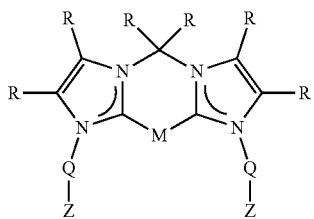
(11)

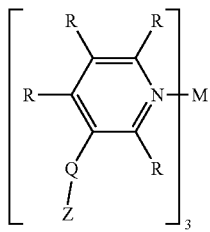
(12)

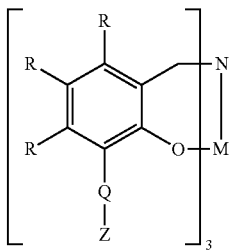
(13)

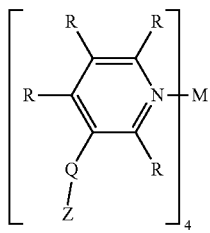
(14)

where, in each of formulas (1)-(13):

each M, A, Q, and Z are as defined in formula (I); and each R is independently —H, $(C_1-C_{40})$hydrocarbyl, $(C_1-C_{40})$heterohydrocarbyl, —Si$(R^1)_3$, —P$(R^1)_2$, —N$(R^1)_2$, —OR$^1$, —SR$^1$, —NO$_2$, —CN, —CF$_3$, R$^1$S(O)—, R$^1$S(O)$_2$—, $(R^1)_2$C=N—, R$^1$C(O)O—, R$^1$OC(O)—, R$^1$C(O)N(R$^1$)—, $(R^1)_2$NC(O)—, or halogen, where each R$^1$ is independently a $(C_1-C_{30})$hydrocarbyl, $(C_1-C_{30})$heterohydrocarbyl, or —H.

8. The supported catalyst of claim 1, wherein the catalytic metal center is selected from the group consisting of chromium, vanadium, magnesium, iron, cobalt, nickel, titanium, zirconium, ruthenium, rhodium, iridium, and palladium.

9. The supported catalyst of claim 1, wherein b is 1, 2, or 3, and each leaving group X is selected from the group consisting of halogens, amines, and amides.

10. The supported catalyst of claim 1, wherein each ligating portion comprises at least one atom coordinated with the catalytic metal center, the at least one atom chosen from carbon, nitrogen, sulfur, oxygen, or phosphorus.

11. The supported catalyst of claim 1, wherein the solid support is chosen from metal oxides, glasses, metals, planar carbon allotropes, and metals or ceramics having charged surfaces.

12. The supported catalyst of claim 1, wherein the solid support is silica, alumina, or a silica-alumina.

13. The supported catalyst of claim 1, wherein the solid support is silica and the surface reactive moiety is tethered to the surface through a Si—O—Si linkage.

14. The supported catalyst of claim 1, wherein the solid support is a metal and the surface reactive moiety comprises a thiol, a thioether, or a thioester.

15. The supported catalyst of claim 1, wherein the solid support is graphite, graphene, carbon nanotubes, or a fullerene and the surface reactive moiety comprises a pyrenyl, an acenyl, or a triptycenyl.

16. The supported catalyst of claim 1, wherein the surface of the solid support is charged and the surface reactive moiety comprises a sulfonate, an ammonium, a pyridinium, a borate, a carboxylate, a thiolate, an imidazolium, a phosphonium, a pyrazolium, or a ferrocenium.

17. A method for oligomerizing ethylene, the method comprising contacting ethylene in a reactor with a supported catalyst according to claim 1.

* * * * *